United States Patent

Braña et al.

Patent Number: 5,554,622
Date of Patent: Sep. 10, 1996

[54] ASYMMETRICALLY SUBSTITUTED BISNAPHTHALIMIDES

[75] Inventors: Miguel F. Braña; José M. C. Berlanga; Marina M. Moset; Maria J. Pérez de Vega, all of Madrid, Spain; Gerhard Keilhauer, Marlboro, Mass.; Xiao-Dong Qian, Wellesley, Mass.; Cynthia Romerdahl, Wayland, Mass.

[73] Assignee: Knoll Aktiengesellschaft, Ludwigshafen, Germany

[21] Appl. No.: 397,259

[22] PCT Filed: Sep. 23, 1993

[86] PCT No.: PCT/EP93/02581

§ 371 Date: Mar. 15, 1993

§ 102(e) Date: Mar. 15, 1993

[87] PCT Pub. No.: WO94/07862

PCT Pub. Date: Apr. 14, 1994

[30] Foreign Application Priority Data

Sep. 30, 1992 [DE] Germany .......................... 42 32 739.3

[51] Int. Cl.$^6$ ................. A61K 31/435; C07D 221/18
[52] U.S. Cl. ............................................ 514/284; 546/76
[58] Field of Search ............................. 546/76; 514/284

[56] References Cited

U.S. PATENT DOCUMENTS 4,841,052  6/1989  Harnisch et al. ...................... 544/361
4,874,863  10/1989  Brana et al. ............................. 540/99
5,086,059  2/1992  Ardecky ................................. 514/284
5,359,070  10/1994  Cherney ................................. 546/76

FOREIGN PATENT DOCUMENTS 281902  9/1988  European Pat. Off. .
WO91/18884  12/1991  WIPO .

OTHER PUBLICATIONS

Petracek F. J. in "Principles of Psychopharmacology" N. G. Clark and J. del Gindice eds. (1970) Academic Press, N.Y. pp. 166–7.

Primary Examiner—C. Warren Ivy
Assistant Examiner—Evelyn Huang
Attorney, Agent, or Firm—Keil & Weinkauf

[57] ABSTRACT

Asymmetrically substituted bisnaphthalimides of the formula I

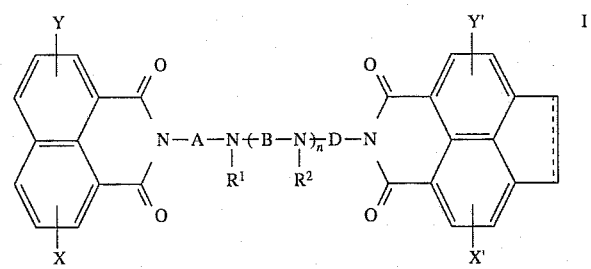

in which A, B, D, $R^1$, $R^2$, m and ‖ have the meanings stated in the description, and the salts thereof with phsiologically tolerated acids, ale described. The novel compounds are suitable for controlling diseases.

2 Claims, No Drawings

ASYMMETRICALLY SUBSTITUTED BISNAPHTHALIMIDES

This application is the national phase of PCT/EP93/02581, filed on Sep. 23, 1993.

The present invention relates to novel asymmetrically substituted bisnaphthalimides, to the preparation thereof and to the use thereof for controlling diseases.

U.S. Pat. No. 4,841,052 discloses compounds in which two naphthalimide residues are connected together via a bridge containing an aromatic residue. These compounds are used as sensitizers in electrophotographic toners. U.S. Pat. No. 4,874,863 describes bisnaphthalimides which are suitable as carcinostatics. Similar is true of the substances of U.S. Pat. No. 5,086,059 which additionally contain ethylene bridges on their naphthalene residues.

The invention relates to asymmetrically substituted bisnaphthalimides of the formula I

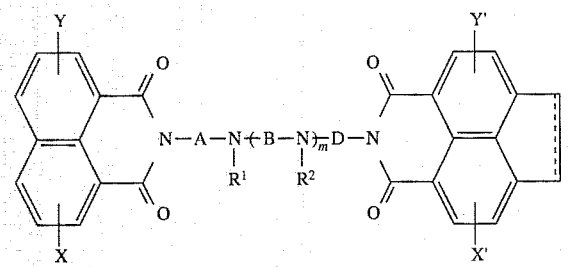

in which

- A, B and D are identical or different and are straight-chain or branched alkylidene groups, cycloalkylidene or phenylene radicals,
- $R^1$ and $R^2$ are identical or different and are hydrogen atoms or $C_1$–$C_6$-alkyl or aryl or benzyl groups which can be substituted by $C_1$–$C_6$-alkyl groups, halogen atoms, $CF_3$—, nitro, hydroxyl, $NR_2^3$, $OR^4$, $COOR^5$, $CONR_2^6$, $CONHR^7$, $NHCOR^8$, $SO_2NHR^9$ or $SO_mR^{10}$ groups, or together are a —$CH_2$—, —$C_2H_4$— or $C_3H_6$— group,
- X, X', Y and Y' are identical or different and are hydrogen or halogen atoms, nitro, amino, $C_1$–$C_6$-alkyl $CF_3$, hydroxyl, $NR_2^3$, $OR^4$, $COOR^5$, CHO, $CONR_2^6$, $CONHR^7$, $NHCOR^8$, $SO_2NHR^9$, $SO_mR^{10}$, $COR^{11}$, ureido, $C_1$–$C_6$-alkylureido, N=C=S or N=C=O groups,
- $R^3$–$R^{11}$ are identical or different and are $C_1$–$C_6$-alkyl, cycloalkyl or aryl groups, m is the number 0, 1 or 2, and ⫽ is a single or double bond, and the salts thereof with physiologically tolerated acids.

Preferred alkylidene groups for A, B and D are those with 1–8 and, in particular, those with 1–4 carbon atoms. Preferred cycloalkylidene radicals are those with 3–7 carbon atoms.

Aryl groups to be particularly mentioned for $R^1$–$R^8$ are phenyl groups. The latter are preferably substituted by 1–2 of the said radicals. Preferred cycloalkyl radicals for $R^3$–$R^{11}$ are those with 3–7 carbon atoms. X and Y are preferably nitro, amino or methyl groups or chlorine atoms and X' and Y' are preferably hydrogen.

The novel compounds can be prepared in accordance with the following reaction scheme:

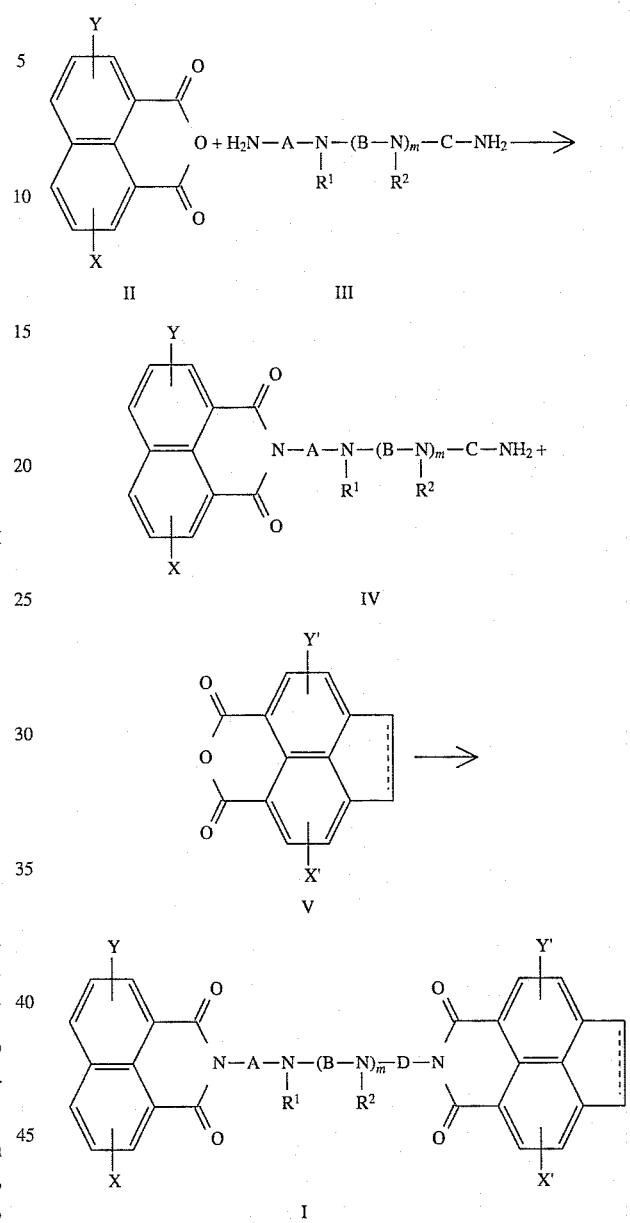

Naphthalic anhydrides II are reacted with one equivalent or with an up to 50% excess of a polyamine III in an organic solvent such as dioxane, ethanol or dimethylformamide at from 20° to 150° C. The solution obtained in this way is concentrated, and the residue is purified, for example, by recrystallization or chromatography. The monoimide obtained in this way is subsequently reacted with the anhydride V, and purified, as described above.

The compounds obtained in this way can subsequently, if required, be converted into their salts with physiologically tolerated acids. To do this, the bases are taken up, for example, in ethanol, dichloromethane or ether, and the salt is precipitated with the acid. Suitable acids are citric acid, tartaric acid, lactic acid, phosphoric acid, alkanesulfonic acids, in particular methanesulfonic acid, acetic acid, formic acid, maleic acid, fumaric acid, malic acid, succinic acid, malonic acid, sulfuric acid, toluenesulfonic acid, L-glutamic acid, L-aspartic acid, pyruvic acid, mucic acid, benzoic acid, glucuronic acid, oxalic acid, ascorbic acid and, in particular, hydrochloric acid.

The starting materials of the formula V with a single bond in the 5-membered ring can be prepared by processes disclosed in the literature (J. Amer. Chem. Soc. 93, 737 (1971)). The corresponding compounds with a double bond in the 5-membered ring are obtained from those with a single bond by the process described for pyracycloquinones in J. Amer. Chem. Soc. 91, (1969) 917.

The polyamines III can be bought or prepared by known processes.

The novel compounds activate non-specific immune cells which kill tumor cells. They can therefore be employed for cancers such as cancer of the bowel, lungs and breast as well as leukemia. They are administered in doses of about 1–500 mg/kg of bodyweight.

The novel compounds have the advantage of being very soluble in water. They can therefore be used much more easily than the known compounds of similar structure.

The following examples are intended to explain the invention in detail. Data in parts or percentages relate in each case to weight.

A. Preparation of the starting materials a. (3-Aminopropyl)[3-(1,8-naphthalimido)propyl]methylamide 2.2 g (0.015 mol) of bis-(3-aminopropyl)methylamine were dissolved in 250 ml of ethanol, and 2.4 g (0.012 mol) of naphthalene-1,8-dicarboxylic anhydride were slowly added over a course of 4 h.

The mixture was subsequently stirred at room temperature for 1 h. The organic solvent was removed under reduced pressure. The remaining oil was purified by flash chromatography ($CH_2Cl_2$/MeOH/$NH_4OH$=4/6/1). 1.7 g (50%) of product [m.p.=266° C. (methanol)] were obtained and were used directly for further reaction.

The following were prepared in a similar way to Aa:

b. N-(2-Aminoethyl)-N'-[2-(1,8-naphthalimido)ethyl]-1,2-diaminoethane, yield 30%, m.p. 137° C. (ethyl acetate).

c. N-(2-Aminoethyl)-N'-[2-(4-chloro-1,8-naphthalimido)ethyl]-1,3-diaminopropane, yield 53%, oil [hydrochloride, m.p. 253° C.].

d. N-(3-Aminopropyl)-N'-[3-(3-hydroxy-1,8-naphthalimido)propyl]-1,4-di(ethylamino)butane, yield 44%, oil.

e. N-[3-(3-Amino-1,8-naphthalimido)propyl](3-aminopropyl)amine, yield 33%, m.p. 190° C.

f. N-(2-Aminoethyl)[2-(4-chloro-1,8-naphthalimido)ethyl]amine, yield 24%, m.p. 280° C. (methanol).

g. N-[3-(3-Amino-1,8-naphthalimido)propyl]-N'-(3-aminopropyl)-1,4-diaminobutane, yield 25%, m.p. 260° C.

h. N-(3-Aminopropyl)[3-(4-chloro-1,8-naphthalimido)propyl]methylamine, yield 37%, oil.

i. N-[3-(3-Amino-1,8-naphthalimido)propyl](3-aminopropyl)methylamine, yeild 32%, m.p. 330° C. (decomposition).

B. Preparation of the final products

Example 1

N-[3-(3-Amino-1,8-naphthalimido)propyl]-N-[3-(5,6-acenaphthimido)propyl]amine 0.7 g (0.0021 mol) of N-[3-(3-amino-1,8-naphthalimido)propyl](3-aminopropyl)amine (from Example Ae) and 0.45 g (0.002 mol) of 5,6-acenaphthenedicarboxylic anhydride were refluxed in 50 ml of ethanol for 2 h. After cooling, the precipitate was filtered off, washed with ethanol and recrystallized from xylene. 0.4 g (38%) of pure substance was obtained, m.p. 205° C.

The substances in the following table were prepared in a similar manner to Example 1:

TABLE

Prepared compounds of the formula I (∥ = single bond)

| Example No. | A | B | D | $R^1$ | $R^2$ |
|---|---|---|---|---|---|
| 2 | $(CH_2)_3$ | — | $(CH_2)_3$ | $CH_3$ | — |
| 3 | $(CH_2)_3$ | — | $(CH_2)_3$ | $CH_3$ | — |
| 4 | $(CH_2)_3$ | — | $(CH_2)_3$ | $CH_3$ | — |
| 5 | $(CH_2)_2$ | $(CH_2)_3$ | $(CH_2)_2$ | H | H |
| 6 | $(CH_2)_2$ | $(CH_2)_2$ | $(CH_2)_2$ | H | H |
| 7 | $(CH_2)_3$ | — | $(CH_2)_3$ | $CH_3$ | — |
| 8 | $(CH_2)_2$ | — | $(CH_2)_2$ | H | — |
| 9 | $(CH_2)_3$ | $(CH_2)_4$ | $(CH_2)_3$ | H | H |
| 10 | $(CH_2)_3$ | $(CH_2)_4$ | $(CH_2)_3$ | $C_2H_5$ | $C_2H_5$ |
| 11 | $(CH_2)_3$ | — | $(CH_2)_3$ | $CH_3$ | — |
| 12 | $(CH_2)_3$ | — | $(CH_2)_3$ | $CH_3$ | — |
| 13 | $(CH_2)_3$ | — | $(CH_2)_3$ | $CH_3$ | — |
| 14 | $(CH_2)_3$ | — | $(CH_2)_3$ | $CH_3$ | — |
| 15 | $(CH_2)_3$ | — | $(CH_2)_3$ | $CH_3$ | — |
| 16 | $(CH_2)_3$ | — | $(CH_2)_3$ | $CH_3$ | — |
| 17 | $(CH_2)_3$ | — | $(CH_2)_3$ | $CH_3$ | — |
| 18 | $(CH_2)_3$ | — | $(CH_2)_3$ | $CH_3$ | — |
| 19 | $(CH_2)_3$ | — | $(CH_2)_3$ | $CH_3$ | — |
| 20 | $(CH_2)_3$ | — | $(CH_2)_3$ | $CH_3$ | — |
| 21 | $(CH_2)_3$ | — | $(CH_2)_3$ | $CH_3$ | — |
| 22 | $(CH_2)_3$ | — | $(CH_2)_3$ | $CH_3$ | — |
| 23*) | $(CH_2)_3$ | — | $(CH_2)_3$ | $CH_3$ | — |

| Example No. | X | X' | Y | Y' | n | m.p. (°C.) | Yield (%) |
|---|---|---|---|---|---|---|---|
| 2 | 4-Cl | H | H | H | 0 | 176 | 78 |
| 3 | 3-$NO_2$ | H | H | H | 0 | 182 | 80 |
| 4 | 2-$CH_3$ | H | H | H | 0 | 96 | 66 |
| 5 | 4-Cl | H | H | H | 1 | 164 | 40 |
| 6 | H | H | H | H | 1 | 202 | 67 |
| 7 | H | H | H | H | 0 | 127 | 60 |
| 8 | 4-Cl | H | H | H | 0 | 211 | 63 |
| 9 | 3-$NH_2$ | H | H | H | 1 | 140 | 30 |
| 10 | 4-OH | H | H | H | 1 | 78 | 68 |
| 11 | 4-$CH_3$ | H | 5-$CH_3$ | H | 0 | 202 | 77 |
| 12 | 4-$NO_2$ | H | H | H | 0 | 189 | 69 |
| 13 | 4-NH-nBu | H | H | H | 0 | 119 | 47 |
| 14 | 3-N=C=S | H | H | H | 0 | 260 | 17 |
| 15 | 3-$NHCOCH_3$ | H | H | H | 0 | 177 | 46 |
| 16 | 3-$NHCOOC_2H_5$ | H | H | H | 0 | 189 | 41 |
| 17 | 4-Br | H | H | H | 0 | 154 | 84 |
| 18 | 3-$NHCOC_6H_5$ | H | H | H | 0 | 234 | 81 |
| 19 | 3-$NO_2$ | H | 6-$NO_2$ | H | 0 | 238 | 41 |
| 20 | 3-$NO_2$ | H | 6-$NH_2$ | H | 0 | 236 | 37 |
| 21 | 3-$NO_2$ | H | 4-Cl | H | 0 | 197 | 29 |
| 22 | 3-$NH_2$ | H | H | H | 0 | 236 | 71 |
| 23*) | 3-$NH_2$ | H | H | H | 0 | 79 | 41 |

*)Compound 23 has a double bond in the five-membered ring (∥ = double bond)

We claim:

1. An asymmetrically substituted bisnaphthalimide of the formula I

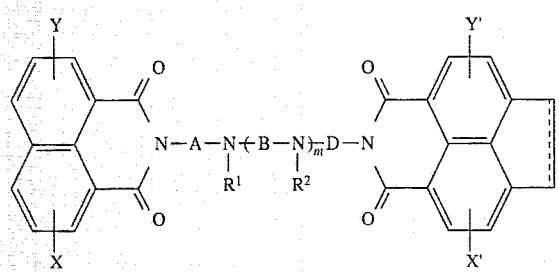

in which
- A, B and D are identical or different and are straight-chain or branched alkylidene groups, cycloalkylidene or phenylene radicals,
- $R^1$ and $R^2$ are identical or different and are hydrogen atoms or $C_1$–$C_6$-alkyl or aryl or benzyl groups which can be substituted by $C_1$–$C_6$-alkyl groups, halogen atoms, $CF_3$—, nitro, hydroxyl, $NR_2^3$, $OR^4$, $COOR^5$, $CONR_2^6$, $CONHR^7$, $NHCOR^8$, $SO_2NHR^9$ or $SO_mR^{10}$ groups, or together are a —$CH_2$—, —$C_2H_4$— or $C_3H_6$— group,
- X, X', Y and Y' are identical or different and are hydrogen or halogen atoms, amino, $C_1$–$C_6$-alkyl, $CF_3$, hydroxyl, $NR_2^3$, $OR^4$, $COOR^5$, CHO, $CONR_2^6$, $CONHR^7$, $NHCOR^8$, $SO_2NHR^9$, $SO_mR^{10}$, $COR^{11}$, ureido, $C_1$–$C_6$alkylureido, N=C=S or N=C=O groups,
- $R^3$–$R^{11}$ are identical or different and are $C_1$–$C_6$-alkyl, cycloalkyl or aryl groups, m is the number 0, 1 or 2, and
- ┆ is a single or double bond, and the salts thereof with physiologically tolerated acids.

2. A pharmaceutical composition comprising a compound of the formula I as defined in claim 1 and a pharmaceutically acceptable carrier.

* * * * *

UNITED STATES PATENT AND TRADEMARK OFFICE
CERTIFICATE OF CORRECTION

PATENT NO.: 5,554,622

DATED: September 10, 1996

INVENTOR(S): BRANA et al.

It is certified that error appears in the above-identified patent and that said Letters Patent is hereby corrected as shown below:

On the cover page, item [57] the Abstract, line 2 after formula I,
"phsiologically" should be --physiologically--.

On the cover page, item [57] the Abstract, line 3 after formula I,
"ale" should be --are--.

On the cover page, item [86], PCT data:
"§ 371 Date: Mar. 15, 1993" should be --§ 371 Date: Mar. 15, 1995--; and
"§ 102(e) Date: Mar. 15, 1993" should be --§ 102(e) Date: Mar. 15, 1995--.

Column 5, claim 1, line 12, ",or" should be -- or--.

Signed and Sealed this

Fourteenth Day of January, 1997

*Attest:*

BRUCE LEHMAN

*Attesting Officer*  *Commissioner of Patents and Trademarks*